United States Patent [19]

Grabowski et al.

[11] 4,301,176

[45] Nov. 17, 1981

[54] METHOD OF ADMINISTERING CALCIUM VALPROATE

[75] Inventors: Albert T. Grabowski, Dover; Sadath U. Khan, Budd Lake, both of N.J.

[73] Assignee: Warner-Lambert Company, Morris Plains, N.J.

[21] Appl. No.: 179,124

[22] Filed: Aug. 18, 1980

[51] Int. Cl.³ .............................................. A61K 31/20
[52] U.S. Cl. ..................................................... 424/318
[58] Field of Search ......................................... 424/318

[56] References Cited

U.S. PATENT DOCUMENTS 3,301,754  1/1967  Meunier .............................. 424/318
3,325,361  6/1967  Meunier ........................... 424/273 R
3,814,812  6/1974  Eymard ............................... 424/318
4,025,649  5/1977  Taillandier et al. ................ 424/318

OTHER PUBLICATIONS

Lachman et al. "Theory and Practice of Industrial Pharmacy", 2nd Ed., 1976 (Lea & Febiger, Phil.) pp. 339-340.

*Primary Examiner*—Frank Cacciapaglia, Jr.
*Attorney, Agent, or Firm*—Stephen I. Miller

[57] ABSTRACT

A chewable anticonvulsant tablet dosage form consisting essentially of calcium valproate and a pharmaceutically acceptable carrier is disclosed. This novel dosage form is conveniently administered and is not irritating to the mucosa of the mouth and throat.

7 Claims, No Drawings

METHOD OF ADMINISTERING CALCIUM VALPROATE

BACKGROUND OF THE INVENTION

Valproic acid is currently marketed in the United States as an anticonvulsant medicament. It is available in the form of a soft gelatin capsule dosage form, and may also be obtained as a syrup containing the sodium salt of valproic acid, i.e., sodium valproate.

The administration of valproic acid has been reported to cause gastro-intestinal side effects including anorexia, nausea and vomiting. Abdominal cramps, diarrhea and constipation have also been observed. Valproic acid is also known to have an irritating effect upon the mucosa of the mouth and throat. The latter effect is such that patients being administered the soft gelatin capsule dosage form are warned as follows: The capsules should be swallowed without chewing to avoid local irritation of the mouth and throat (see Physicians Desk Reference, page 512, 34th ed; 1980, Medical Economics Company, Oradell, N.J. 07649). This untoward characteristic is an obvious disadvantage to the administration of the soft gelatin capsule dosage form. This characteristic is a particular problem when the dosage form is intended to be administered to pediatric and geriatric patients; since many of these classes of patients are either incapable of understanding the precautionary instructions or are not able to swallow the capsule. The syrup dosage form (sodium valproate) has the attendant problems of being, (1) inconvenient to use since the proper volume to deliver the necessary dose must be individually measured for each administration; and (2) being non-portable since a container of liquid as well as a measuring device must be transported. These problems are particularly troublesome for self administration by a pediatric or geriatric patient.

It should also be noted that since sodium valproate is a hygroscopic material, the production of a compacted dosage form (tablet) containing this substance is precluded.

It is therefore clear that it would be desirable to provide an improved oral dosage form for the administration of this medicament.

SUMMARY OF THE INVENTION

The invention sought to be patented in its principle composition aspect is a chewable anticonvulsant tablet dosage form which consists essentially of the calcium salt of valproic acid, i.e., calcium valproate, and a pharmaceutically acceptable carrier.

The invention sought to be patented in its method aspect consists of a method for treating a human being suffering from convulsions, which comprises administering to said human being the chewable anticonvulsant tablet dosage form of the invention.

DESCRIPTION OF THE PREFERRED EMBODIMENTS

In practice, calcium valproate is mixed with a suitable proportion of a pharmaceutically acceptable carrier having the necessary binding properties. The thus obtained tablet mix (granulation) is thereafter compacted into chewable tablets of the desired shape and size.

Formation of the tablet is accomplished by subjecting the granulation to high pressures by moveable punches operating in a die wherein the granulation is confined. This procedure is well known to those skilled in the art.

The finished tablet will preferrably contain from about 5 to 10 to about 50 percent of calcium valproate.

The calcium valproate is conveniently prepared from valproic acid (see for example U.S. Pat. No. 3,814,812) which itself may be readily prepared (see for example U.S. Pat. No. 1,873,732) or may be obtained commercially.

The pharmaceutically acceptable carrier contemplated by the invention may be one or more substances which may, in addition, function as diluents, stabilizing agents, flavoring agents, solubilizers, lubricants, suspending agents, binding agents, or tablet-disintegrating agents.

Suitable solid carriers are magnesium carbonate, magnesium stearate, calcium stearate, talc, mannitol, powdered sugar, sugar, lactose, pectin, dextrin, starch, gelatin, tragacanth, methyl cellulose, sodium carboxymethyl cellulose, polyvinylpyrrolidone, a low melting wax, cocoa butter, and the like; as well as mixtures thereof. It has been found that a particularly suitable diluent is powdered sugar and more specifically a fondant-size or fondant type sugar (powdered confectioner's sugar) which may be produced by the method of U.S. Pat. No. 3,365,331.

The choice of the pharmaceutically acceptable carrier component(s), the proper quantities thereof, and the method of their combination with the calcium valproate to yield a granulation possessing the desired characteristics for compaction is within the skill of the art.

The weight of calcium valproate incorporated in the finished chewable tablet must be such as to provide the desired dosage of valproic acid. Thus, for example, 148.1 mg of calcium valproate is incorporated in a chewable tablet designed to provide a dosage of 125 mg valproic acid. Similarly, 296.2 mg of calcium valproate is incorporated in a chewable tablet designed to provide a dosage of 250 mg valproic acid.

The following non-limiting examples illustrate the best mode contemplated by the inventors for carrying out their invention.

EXAMPLE I

|  | Each Tablet |
| --- | --- |
| Calcium Valproate (Equivalent to 125 mg Valproic Acid) | 148.1 mg |
| Powdered Sugar | 200–600 mg |
| Mannitol USP | 200–600 mg |
| Polyvinylpyrrolidone USP | 5–50 mg |
| Calcium Stearate | 1–10 mg |
| Oil of Peppermint | 0.005–0.10 mg. |
| Purified Water q.s. or | .01–.06 ml |
| Tablet Weight | 750–1400 mg |

Procedure:

Mix the calcium valproate, powdered sugar and mannitol, pass through a suitable mill. Dissolve the polyvinylpyrrolidone in a small amount of water, add to the milled powders, mix to produce a granulation. Dry in an oven overnight. Pass the dried granulation through a suitable mill, add the oil of peppermint flavor and blend well. Compress tablets at a weight to provide the equivalent of 125 mg valproic acid.

The variable quantities are to be adjusted based on the quantity of drug in order to give the desired tablet weight.

EXAMPLE II

| | Each Tablet |
|---|---|
| Calcium Valproate | 296.2 mg |
| (Equivalent to 250 mg Valproic Acid) | |
| Powdered Sugar | 300–1000 mg |
| Mannitol USP | 200–1200 mg |
| Polyvinylpyrrolidone USP | 10–100 mg |
| Magnesium Stearate | 2–20 mg |
| Oil of Spearmint | .010–0.20 mg |
| Purified Water q.s. or | .02–0.12 ml |
| Tablet Weight | 1000–2700 mg |

These tablets are prepared by the procedure described in Example I.

EXAMPLE III

By following the procedure described in Example I, one thousand chewable calcium valproate tablets each containing 148.1 mg calcium valproate are prepared from the following receipe.

| | |
|---|---|
| 1. Calcium Valproate, q.s. | *148.10 g |
| 2. Powdered Sugar q.s. or | 400.00 g |
| 3. Mannitol USP q.s. or | **476.30 g |
| 4. Polyvinylpyrrolidone USP q.s. or | 25.00 g |
| 5. Purified Water q.s. or | 40.00 ml |
| 6. Calcium Stearate NF Powder q.s. or | 8.50 g |
| 7. Blended Fruit Flavor flavor q.s. or | 2.10 g |
| TO MAKE: | 1060.00 g |

*Equivalent to 125 mg of Valproic Acid - Amount to be adjusted based on the drug assay (dry basis).
**Amount to be adjusted based on the quantity of drug in order to give tablet weight of 1060 mg.

The tablet formulations may be varied to produce products containing an amount of calcium valproate which is the equivalent of virtually any weight of valproic acid. The preferred range being about 25 mg to about 250 mg valproic acid. A wide range of tablet flavoring agents may be used, with added synthetic or natural sweeteners if desired. The chewable tablets may also be colored with a variety of approved colorants.

Further, it will be apparent to those skilled in the art that the chewable tablets of the present invention may also be produced as multilayer tablets which may contain additional compatible medicaments, if desired. Methods for producing multilayer tablets are well known to those skilled in the art. The chewable tablets of the invention may also have various different shapes and sizes. Further, these tablets, once formed, may be coded and/or coated by a variety of procedures well-known to those skilled in the art.

We claim:

1. A method of treating a human being suffering from convulsions, which comprises administering to said human being, a chewable anticonvulsant tablet dosage form consisting essentially of calcium valproate and a pharmaceutically acceptable carrier.

2. The method as defined in claim 1 wherein said dosage form; consists essentially of calcium valproate, powdered sugar, mannitol, polyvinylpyrrolidone, calcium stearate and a flavoring agent.

3. The method as defined in claim 2 wherein the calcium valproate is present in said dosage form in an amount equivalent to about 125 mg of valproic acid.

4. The method as defined in claim 2 wherein the calcium valproate is present in said dosage form in an amount equivalent to about 250 mg of valproic acid.

5. The method as defined in claim 3 wherein the flavoring agent is oil of peppermint or oil of spearmint.

6. The method as defined in claim 4 wherein the flavoring agent is oil of peppermint or oil of spearmint.

7. A method as defined in claim 1, whereby irritation of the mouth and throat is avoided.